United States Patent [19]

Noishiki et al.

[11] Patent Number: 5,171,261
[45] Date of Patent: Dec. 15, 1992

[54] VASCULAR PROSTHESIS, MANUFACTURING METHOD OF THE SAME, AND SUBSTRATE FOR VASCULAR PROTHESIS

[75] Inventors: Yasuhara Noishiki, Tottori; Teruo Miyata, Tokyo, both of Japan

[73] Assignee: Koken Co., Ltd., Tokyo, Japan

[21] Appl. No.: 508,618

[22] Filed: Apr. 13, 1990

[30] Foreign Application Priority Data

Apr. 17, 1989 [JP] Japan .................................. 1-95238
Dec. 28, 1989 [JP] Japan ................................. 1-338543

[51] Int. Cl.$^5$ .............................................. A61F 2/06
[52] U.S. Cl. ......................................... 623/1; 600/36
[58] Field of Search ............... 623/1, 12, 15; 600/36; 435/240.241, 240.242

[56] References Cited

U.S. PATENT DOCUMENTS

| | | | |
|---|---|---|---|
| 3,986,828 | 10/1976 | Hoffman, Jr. et al. | 623/1 |
| 4,061,134 | 12/1977 | Samuels et al. | 623/1 |
| 4,553,272 | 11/1985 | Mears | 623/1 |
| 4,581,028 | 4/1986 | Fox, Jr. et al. | 623/16 |
| 4,804,381 | 2/1989 | Turina et al. | 623/1 |
| 4,804,382 | 2/1989 | Turina et al. | 623/1 |
| 4,806,595 | 2/1989 | Noishiki et al. | 623/1 |
| 4,816,028 | 3/1989 | Kapadia et al. | 623/1 |
| 4,822,361 | 4/1989 | Okita et al. | 623/1 |
| 4,842,575 | 6/1989 | Hoffman et al. | 600/36 |

Primary Examiner—Randy C. Shay
Attorney, Agent, or Firm—Varndell Legal Group

[57] ABSTRACT

The invention relates to a vascular prosthesis wherein, fragments of biological tissues such as vascular tissues, connective tissues, fat tissues and muscular tissues and/or cells composing vascular walls such as vascular endothelial cells, smooth muscle cells and fibroblast cells are deposited and captured within the wall of a vascular prosthesis substrate; a manufacturing method comprising the steps of immersing a vascular prosthesis substrate into a dispersed solution of fragments of biological tissues such as vascular tissues, connective tissues, fat tissues and muscular tissues and/or cells composing vascular walls such as vascular endothelial cells, smooth muscle cells and fibroblast cells, and depositing and capturing the cells and/or tissue fragments on the inner wall and within the wall of the vascular prosthesis from one side to the other side of the vascular prosthesis substrate wall by providing a pressure differential between the outside and the inside of the vascular prosthesis substrate; and a substrate suitable for manufacturing a vascular prosthesis having a porous membrane having pores capable of trapping tissue fragments, or a laminate structure with such a membrane and another porous membrane having pores not large enough to pass the cells or tissue fragments.

3 Claims, 1 Drawing Sheet

VASCULAR PROSTHESIS, MANUFACTURING METHOD OF THE SAME, AND SUBSTRATE FOR VASCULAR PROTHESIS

BACKGROUND OF THE INVENTION

1. Field of the Invention

The present invention relates to a vascular prosthesis, methods of manufacturing such a prosthesis and to a substrate suitable for manufacturing the prosthesis. More particularly, the invention relates to a vascular prosthesis having tissue fragments and/or cells adhered to and captured within the wall of the prosthesis, to methods of manufacturing such a vascular prosthesis and to substrates suitable for manufacturing such vascular prostheses.

2. Description of Prior Art

Various vascular prostheses are known. Some are made of synthetic polymers such as polytetrafluoroethylene or polyester. Others are made of human cord veins, animal blood vessels and of various biological tissues crosslinked with glutaraldehyde as the crosslinking agent. When such vascular prostheses are placed in a mammalian or human body, the inner walls of the prostheses become coated with endothelial cells, which possess antithrombotic properties for preventing blood clotting and deposition of thrombus on the inner walls.

In actual clinical applications, however, coating by the endothelial cells is usually extremely delayed and, in most cases, only the area of the anastomosis of the vascular graft becomes covered with endothelial cells while positions remote from the anastomosis are not covered. Accordingly, thrombus deposits form the inner wall of the vascular prosthesis, blocking the vascular graft.

In order to prevent this problem, it is known to introduce endothelial cells onto the inner wall of the vascular graft in advance. For example, endothelial cells cultivated in vitro are deposited onto the inner wall of the prosthesis by various techniques. However, when a prosthesis so obtained is transplanted into the body of a mammal, the graft is dilated by blood pressure, causing cracks in the cell deposits. The cells can then separate and be washed away by the blood flow. As a result, this technique has not been clinically applied.

SUMMARY OF THE INVENTION

It is an object of the invention to provide a substrate suitable for obtaining vascular prostheses free from the above defects having various tissue fragments and/or cells deposited and captured within the walls of the prosthesis.

It is an additional object of the invention to provide a vascular prosthesis obtained by depositing and capturing various tissue fragments and/or cells within walls of such a suitable substrate.

It is a further object of the invention to provide a method of manufacturing vascular prostheses having various tissue fragments and/or cells deposited and captured on and within the walls of the prosthesis.

To achieve the above objects, the invention of the present application relates to a vascular prosthesis where fragments of biological tissues such as vascular tissue, connective tissues, fat tissues and muscular tissues; cells of vascular walls such as vascular endothelial cells, smooth muscle cells or fibroblast cells; and mixtures of biological tissue fragments, mixtures of vascular wall cells or mixtures of biological tissue fragments and vascular wall cells are deposited and captured at least within a wall of the vascular prosthesis substrate. The term "and/or" as used throughout this specification is meant to encompass various combinations.

In order to further achieve the above objects, a manufacturing process is described which comprises the steps of immersing a vascular prosthesis substrate in a disperse solution of fragments of biological tissues such as vascular tissues, connective tissues, fat tissues and/or cells composing vascular walls such as vascular endothelial cells, smooth muscle cells or fibroblast cells, and depositing and capturing the cells and/or tissue fragments within the walls of the prosthesis substrate by providing a pressure differential between the inside and the outside of the prosthesis substrate.

In order to further achieve the above objects, a substrate suitable for manufacturing such a vascular prosthesis is described. The substrate can comprise a porous membrane having pores capable of trapping tissue fragments or cells therein. The substrate can be a laminate structure of such a porous membrane and another porous membrane having pores not large enough to allow the tissue fragments or cells to pass through.

The biological tissue fragments and/or cells comprising the blood vessel described herein are deposited and captured on and within the wall of the prosthesis and can extend from one side to the other side of the wall. This concept differs from the prior art technique of depositing cells only on the inner surface of the vascular prosthesis.

In the present invention, the biological tissue fragments and/or cells are introduced through the mesh structure of the substrate of the vascular prosthesis from outside or inside of the vascular prosthesis and, therefore, they are entangled within the mesh structure of the wall of the vascular prosthesis. Accordingly, in spite of high blood pressure or rapid blood flow, peeling of tissue fragments or cells, or cracks among cells can be avoided and, moreover, unlike a conventional cloth-made vascular prosthesis, the prosthesis of the present invention is free from preclotting operations such as treating with blood to form a rigid fibrin layer.

Furthermore, in the present invention, when the patient's (i.e., a mammal including humans) own tissues are used as tissue fragments and vascular wall cells, the procedure represents an autograft and is completely free from rejection by the patient's body, so that a preclotting operation is not needed.

DETAILED DESCRIPTION OF THE INVENTION

The invention is described in further detail below.

First, the vascular prosthesis substrate according to the present invention is described. Materials comprising the substrate for the vascular prosthesis of the invention are not particularly limited and may include, among others, polyester, nylon, polyurethane, polytetrafluoroethylene, polycarbonate, polyacetate, polyvinyl alcohol, cellulose derivatives and other fibers made into tubular structures by weaving or knitting or by nonwoven membrane forming. The substrate can also comprise a porous tubular structure formed by drawing, for example, polytetrafluoroethylene tubing.

Figure 2:
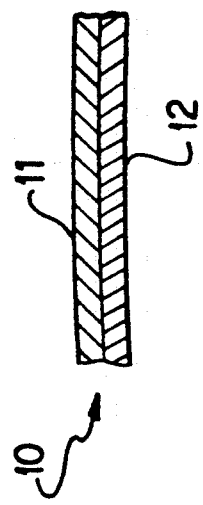
FIG. 2 is a cross sectional view of a portion of a laminated substrate according to the present invention.

The substrate for the vascular prosthesis may be structured either as a single layer of porous membrane having pores capable of trapping cells or tissue fragments, or as a double layer structure comprising such a porous membrane, together with another porous membrane having holes or pores not large enough to allow the cells or tissue fragments to pass therethrough. A portion of a double layer or laminated substrate 10 is shown in FIG. 2 where layer 11 is a porous membrane capable of trapping cells or tissues fragments and layer 12 is a porous membrane impermeable to passage of cells or tissue fragments therethrough.

The size of the pores capable of trapping tissue fragments varies with the size of fragments and, generally, these pores should have a permeability corresponding to at least 400 cc.min/cm$^2$.120 mmHg. The size of pores not large enough to permit passing of the cells or tissue fragments therethrough generally have a permeability corresponding to at most 300 cc.min/cm$^2$.120 mmHg.

The permeability is expressed as the passing of the given volume of water per unit area of 1 cm$^2$ per minute at a water pressure corresponding to 120 mmHg, and the porous membranes can be classified into three grades by their permeability. The grade with a permeability of 400 cc.min/cm$^2$.120 mmHg or less is a low porous membrane; the grade with a permeability of 400 to 1800 cc.min/cm$^2$.120 mmHg is a medium porous membrane, and the grade with a permeability over 1800 cc.min/cm$^2$.120 mmHg is a high porous membrane. In the present invention, substrates for vascular prostheses can include the medium or high porous membranes when used in a single layer structure. In a double layer laminate structure, the medium or high porous membranes can be used for the outer side or layer and the low porous membranes can be used for the inner side or layer, or the medium or high porous membranes can be used for the inner side or layer and low porous membrane can be used for the outer side or layer.

As is apparent in this description, the term "membrane" is not limited. This term is inclusive of biologically acceptable materials of cloth, whether these materials are woven, knitted or otherwise manufactured. This term also encompasses materials other than cloth, whether woven or otherwise manufactured, the criteria being that the materials are porous with a permeability as described above, and that said materials will trap or otherwise capture tissue fragments and vascular cells as described within this disclosure.

As noted, substrates for vascular prostheses can be manufactured by weaving or knitting fibers, or can be membranes of nonwoven cloth; but in the case of a substrate having a double layer structure it is preferred to manufacture only one side or layer by such methods, and to use a low porous membrane made by weaving fine fibers for the other side or layer.

In the substrate for the vascular prosthesis of the invention, the outer surface or layer can be made of non-absorbing material and the inner surface or layer can be made of bio-absorbing material. Examples of bio-absorbing material include collagen, polylactic acid, polybutyric acid, chitin-chitosan, or their derivatives.

The vascular prosthesis of the present invention has the biological tissue fragments or cells deposited thereon and captured therein in a manner so that the biological tissue fragments or cells are deposited and captured within the wall and/or on the inner surface of the vascular prosthesis substrate. This promotes the growth of endothelial cells and, in particular, by the depositing and capturing autotissue fragments, it is possible to provide environments advantageous for the formation of endothelial cells on the inner surface of the vascular prosthesis. It is therefore desirable to collect tissue fragments or cells from the host mammal near the transplatation, and then disperse the collected tissue fragments or cells in an isotonic solution suited to the preservation of the collected cells and tissue fragments, such as a physiological saline solution. The collecting and culturing of the tissue fragments and/or cells can be carried out in a well-known manner. Thereafter, the isotonic solution of collected cells and/or tissue fragments is used in the manufacture of the vascular prostheses of the invention. When the substrate of the vascular prosthesis has a double layer structure, by providing one side or layer with a coarse mesh structure and the other side or layer with a fine porous structure, the tissue fragments and/or cells can be efficiently trapped within the vascular prosthesis.

The manufacturing method according to the invention comprises the steps of immersing the substrate for the vascular prosthesis in a disperse solution of biological tissue fragments such as vascular tissues, connective tissues, fat tissues and muscular tissues and/or cells such as vascular endothelial cells, smooth muscle cells and fibroblast cells; and depositing and capturing the cells and/or tissue fragments within the wall and on the inner surface of the vascular prosthesis substrate wall from the outside and/or the inside of the vascular prosthesis substrate by providing a pressure differential between the outside and the inside of the substrate. The interior space of the vascular prosthesis can be vacuumized or can be pressurized, and the cells and/or tissue fragments are deposited and captured in and on the walls either outside or inside of the prosthesis substrate.

In the present invention, it is desired to use the substrates as mentioned above, but the present invention is not particularly necessary to these substrates. Especially when capturing tissue fragments, it is sufficient to use a high porous layer alone, and a low porous layer is not necessarily required on the inner surface of the high porous layer.

For convenience of handling, it is preferable to use fragments of biological tissues of about 3 mm or less. Such fragments or cells are dispersed in physiological saline solution at a concentration of less than 50 wt/wt %.

The substrate for the vascular prosthesis is immersed in the dispersed solution, and a pressure differential is provided between the inside and the outside of the substrate. For example, the substrate is immersed in the dispersed solution of tissue fragments or cells, and the interior of the prosthesis substrate is vacuumized. Alternatively, the substrate can be placed into a flexible bag filled with the dispersed solution of tissue fragments or cells, and pressure is applied from outside.

Figure 1:
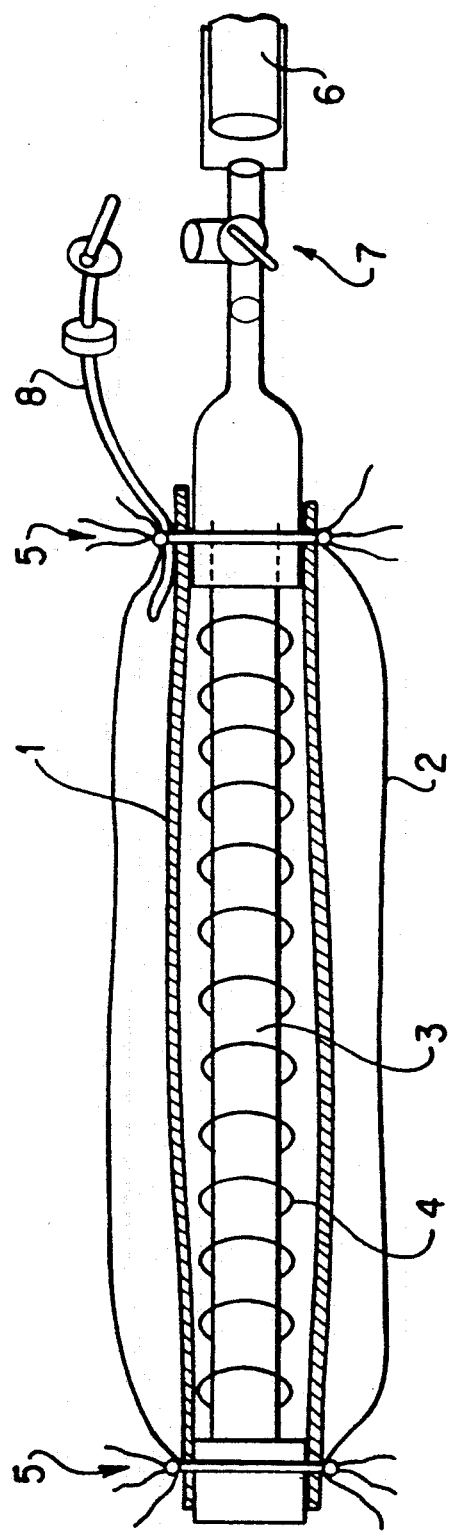
FIG. 1 is an explanatory drawing of a manufacturing method for making a vascular prosthesis according to the invention.

FIG. 1 is an explanatory drawing of an assembly which can be used in the manufacturing method of the present invention. In the figure, a substrate for a vascular prosthesis 1 is provided within a transparent bag 2, such as a polyvinyl chloride bag. A vinyl chloride or silicon tube 3 which can have an undulating surface formed, for example, by spirally winding a wire 4 about the surface of the tube 3 is provided within the substrate 1. The tube 3 has one closed end and numerous tiny holes therein for permitting a pressure differential to be established through the substrate 1. The ends of the bag 2 are closed by, for example, a ties 5, so as to enclose both ends of the substrate 1 about ends of the tube 3. The other end of the tube 3 is connected to syringe 6 through a stopcock 7. A piston having a stem (not shown) can be provided in the syringe 6 for applying a vacuum or pressure within tube 3 and thereby to the inner surface of substrate 1 by pulling or pushing the piston within syringe 6. A tube 8 of, for example, silicon rubber can be inserted between the bag 2 and the substrate 1 at the end thereof next to the stopcock and secured with tie 5. With this arrangement, an inner-outer bag assembly is provided for subjecting the substrate 1 to a pressure differential perpendicular to its surface, namely in an radial direction. For example, tube 8 can be used for supplying cells or tissue fragments to the exterior of substrate 1 and interior portion of the inner bag 2 can be placed under a vacuum through action of syringe 6 and stopcock 7 or the like, so that the entire assembly can be uniformly subjected to a vacuum. Alternatively, tube 8 can be connected a vacuum source for creating a lower pressure on the exterior of substrate 1 when compared to the interior of substrate 1, and cells or tissue fragments can be supplied from syringe 6 through stopcock 7. Further, a combination of the above two procedures of alternatively placing one of the interior or exterior of substrate 1 under a lower pressure relative respectively to the exterior or interior of the substrate 1, and then placing the other of the interior or exterior of the substrate 1 under a lower pressure relative respectively to the exterior or interior of the substrate 1, can also be used.

The above-described inner-outer bag assembly can also be operated by slightly opening the stopcock 7 before the syringe 6, supplying cells or tissue fragments to the exterior of substrate 1 through tube 8, and rubbing bag 2 by hand to pressurize the bag 2. This results in the cells or tissue fragments being deposited and captured within the walls of the vascular prosthesis substrate 1.

The vascular prosthesis of the invention need not only be used as a mere substitute for blood vessels, but also as prosthetic materials for filling up defective position of the body such as myocardium and peritoneum, by cutting the vascular prosthesis open into a membranous form.

DESCRIPTION OF THE PREFERRED EMBODIMENTS

EXAMPLE 1

A fibrous collagen solution was applied to the inner surface of a polyester cloth tube with an inside diameter of 8 mm, a length of 50 mm, and a porosity of 1800 cc/cm$^2$.120 mmHg and dried in air. A vascular prosthesis substrate having an inner layer of a low porosity membrane of collagen was formed. The collagen was crosslinked to be insoluble by using a polyepoxide crosslinking agent rather than the glutaraldehyde of the prior art. Representative polyepoxy crosslinking agents which can be used in the present invention include polyglycidyl ethers of glycerols (polymerization degree of 1-3), polyglycidyl ethers of polyols and, in particular, glycerol diglycidyl ether, glycerol triglycidyl ether, diglycerol tetraglycidyl ether, and ethyleneglycol glycidyl ether. In this example, polyethylene glycol diglycidyl ether having a polymerization degree of 1 (Denacol EX-810, Nagase Kasei Kogyo K.K., Osaka) was used.

The rate of crosslinking is measured as a rate of reaction of $\epsilon$-amino groups on the side chains of the collagen. By adjusting the rate of crosslinking, collagen membranes can be obtained, having various degrees of solubility or biodegradability after implantation.

One end of the prosthesis substrate was ligated and a vinyl chloride tube was inserted from the other, and while applying a vacuum to the interior of the vinyl chloride tube, the prosthesis was placed into an endothelial cell suspension, thereby accumulating and capturing a great quantity of endothelial cells above the collagen membrane, namely, between the collagen membrane and the polyester cloth tube. The polyester cloth tube assisted in holding the endothelial cells in place, because endothelial cells are trapped and held by the pores of the polyester cloth tube. Optical microscopic findings disclosed that the endothelial cells were gathered at high concentrations by this procedure. After loosening the ligated end of the prosthesis, the prepared vascular prosthesis was implanted in the thoracic descending aorta of a grown dog. After implanting, the endothelial cells were not washed away. Three weeks after the implant, numerous colonies of endothelial cells were observed in the inner surface of the vascular prosthesis, and deposits of thrombus were not noted. Three months after implanting, the collagen membrane disappeared, the inside of the vascular prosthesis was completely covered with endothelial cells, and multiple fibroblast cells invaded the neoplastic vascular wall. Capillary vessels also invaded to form a new vascular wall.

EXAMPLE 2

Using the method of Example 1, a fibroblast suspension was used in place of the endothelial cells of Example 1. Fibroblasts were accumulated and captured above the collagen membrane inside a vascular prosthesis in the same manner as in Example 1. The vascular prosthesis was implanted into the thoracic descending aorta of a grown dog. Immediately after implanting, the inside surface was covered with a fresh fibrin layer, but above the collagen membrane, the fibroblasts were not washed away. Three weeks after implanting, innumerable fibroblasts were seen inside the prosthetic vascular wall, and invasion of capillary vessels from outside was also noticed. The inside wall in the vicinity of the anastomosis was already covered with endothelial cells, and multiple smooth muscle cells, fibroblasts and capillary vessels were noted inside the wall.

EXAMPLE 3

Using the operations of Example 2, smooth muscle cells were used instead of fibroblasts. Smooth muscle cells were accumulated above the collagen membrane inside the vascular prosthesis. When this vascular prosthesis was implanted in the thoracic descending aorta of a grown dog, results similar to Example 2 were obtained.

EXAMPLE 4

Using the method of Example 1, a mixed culture broth of endothelial cells and fibroblasts was used instead of the endothelial cells of Example 1. Fibroblasts and endothelial cells were accumulated and captured above the collagen membrane inside the vascular prosthesis. This vascular prosthesis was implanted in the thoracic descending aorta of a grown dog, and results similar to Example 1 were obtained.

EXAMPLE 5

Using the method of Example 1, a mixed culture broth of endothelial cells and smooth muscle cells was used instead of the endothelial cells of Example 1. Fibroblasts and smooth muscle cells were accumulated and captured above the collagen membrane inside the vascular prosthesis. This vascular prosthesis was implanted in the thoracic descending aorta of a grown dog, and similar results were obtained.

EXAMPLE 6

A tubular substrate was prepared by applying a fibrous collagen solution to the inside surface of a polyester cloth vascular prosthesis measuring 4 mm in inside diameter and 6 mm in length, and was dried in air to form a porous membrane of collagen. The collagen was impregnated with protamine sulfate solution, and was crosslinked to be insoluble by using a polyepoxy compound (Denacol EX-810, Nagase Kasei Kogyo K.K., Osaka). It was then put into a heparinized solution to apply protamine to the inside collagen membrane to be bonded with heparin ions (See U.S. Pat. No. 4,806,595 which is incorporated herein by reference). By this operation, the inner surface was endowed with the antithrombotic property of heparin sustained-slow release agent.

One end of the substrate was ligated, a vacuum was applied from the other end, and the prosthesis put into an endothelial cell suspension. Endothelial cells were abundantly accumulated and captured above the collagen membrane. Optical microscopic findings disclosed that endothelial cells were collected at high concentration by this operation.

The ligation was removed and the vascular prosthesis was implanted in the carotid artery of a grown dog. Immediately after implantation, the interior surface was completely free from thrombus deposit, and the endothelial cells were not washed away and remained in place above the collagen membrane. Three weeks after implantation, innumerable colonies of endothelial cells were observed inside the vascular prosthesis, and deposit of thrombus was not noticed.

Three months after implantation, the collagen membrane disappeared, the inside of the vascular prosthesis was completely covered with endothelial cells, and multiple fibroblasts invaded the neoplastic vascular wall, as did capillary vessels, and a new vascular wall was completed.

EXAMPLE 7

Using fibroblasts in place of the endothelial cells of Example 6 and using the same procedures as Example 6, fibroblasts were accumulated and captured inside the vascular prosthesis.

The vascular prosthesis was implanted in the carotid artery of a grown dog, and an anticlotting therapy was given for three weeks during and after implantation. As a result, immediately after implantation, deposit of thrombus was not observed on the collagen membrane inside the vascular prosthesis. Above the collagen membrane, the fibroblasts present at the time of implantation were not washed away, an invasion of capillary vessels from the outer membrane side was noted, and a covering of endothelial cells was already noted in the vicinity of the anastomosis. Three months after implantation, the collagen membrane was completely eliminated, and the inside of the vascular prosthesis was completely covered with endothelial cells. Inside the wall, multiple smooth muscle cells, fibroblasts and capillaries were noted, and a new vascular wall was formed.

EXAMPLE 8

Instead of the fibroblasts of Example 7, smooth muscle cells were used in the same manner as in Example 7. Smooth muscle cells were accumulated and captured above the collagen membrane inside the vascular prosthesis.

The thus prepared vascular prosthesis was implanted in the carotid artery of a grown dog, and an anticlotting therapy was given for three weeks during and after implantation. As a result, right after implantation, thrombus deposit was not seen on the collagen membrane inside the vascular prosthesis. Above the collagen membrane, the smooth muscle cells present at the time of implantation were not washed away. Three weeks after implantation, numerous smooth muscle cells were observed in various positions in the vascular prosthesis, an invasion of capillary vessels from the outer membrane side was noted, and a covering of endothelial cells was noted inside in the vicinity of the anastomosis. Three months after implantation, the collagen membrane was completely covered with endothelial cells. Inside the wall, multiple smooth muscle cells, fibroblasts and capillary vessels were observed, and a new vascular wall was completed.

EXAMPLE 9

A vascular prosthesis was prepared as in Example 6, except that a mixed culture broth of endothelial cells and fibroblasts was used instead of the endothelial cells in Example 6. The prosthesis was implanted in the carotid artery of a grown dog as in Example 6, and immediately after implantation no thrombus formation or deposit was noted. Three months after implantation, the collagen membrane had disappeared, the inside of the vascular prosthesis was completely covered with endothelial cells, and multiple fibroblasts invaded into the neoplastic vascular wall, as did capillary vessels.

EXAMPLE 10

Using the procedures of Example 9, a mixed culture broth of endothelial cells and smooth muscle cells was used in place of the mixed culture broth of endothelial cells and fibroblasts. The vascular prosthesis thus prepared was implanted in the carotid artery of a grown dog. Three months after implantation, a new vascular wall was completed.

EXAMPLE 11

One end of a polyester cloth vascular prosthesis of 8 mm inside diameter, 5.7 cm in length and 1800 $cc/cm^2$.120 mmHg in porosity was ligated. About 5 g of subcutaneous connective tissues were collected from a grown dog, cut into small pieces by a surgical knife in a Petri dish, a physiological saline solution was added, and a connective tissue fragment suspension was thus prepared. The vascular prosthesis ligated at one end was placed into this solution, and a vacuum was applied from the other end in order to deposit a large volume of connective tissue fragments in the wall of the vascular prosthesis. By optical microscopic examinations, it was observed that connective tissue fragments having countless fibroblasts and capillary vessels were abundantly captured by this operation within the gaps of fibers of the vascular prosthesis.

The vascular prosthesis was implanted in the thoracic descending aorta of the same grown dog from which the subcutaneous connective tissues were collected. Immediately after implantation, the tissue fragments were not washed away. A thin layer of fresh thrombus and fibrin were deposited on the inner wall. Three weeks after implantation, there were colonies of endothelial cells inside the vascular prosthesis, and numerous fibroblasts and capillary vessels were noted inside the prosthetic vascular wall. Three months after implantation, the inner surface was completely covered with an endothelial cell layer, and innumerable smooth muscle cells, fibroblasts and capillary vessels invaded into the neoplastic vascular wall, and a new vascular wall was thus completed.

EXAMPLE 12

Five pieces of venous sections of 3 to 4 cm in length were collected from a grown dog. In this case, varix may be formed in the venous pieces, or very thin pieces without branches in the peripheral area could also be sampled. These pieces were cut into small sections by using a surgical knife in a Petri dish, a physiological saline solution was added, and a venous tissue fragment suspension was thus prepared.

One end of a polyester vascular prosthesis substrate having a fine mesh structure with surfaces made fluffy by abrasion having a high porous surface outside and medium porous surface inside, and with an inside diameter of 8 mm, a length of 5.7 cm and a water porosity of 1800 cc/cm$^2$.120 mmHg was ligated, put into the prepared venous tissue fragment suspension, and a vacuum was applied to the inner space from the other end, thereby abundantly depositing and capturing tissue fragments inside the prosthetic vascular wall. By optical microscopic examination, it was observed that venous tissue fragments having innumerable endothelial cells, smooth muscle cells and fibroblasts were abundantly captured in the gaps or pores between the fibers of the prosthesis, especially at the inner surface side.

The vascular prosthesis was implanted in the thoracic descending aorta of the same grown dog from which the venous sections where collected, and immediately after implantation, the tissue fragments were not washed away. In the inner surface, a thin layer of fresh thrombus and fibrin was deposited. Three weeks after implantation, there were multiple colonies of endothelial cells inside the vascular prosthesis, and countless fibroblasts and capillary vessels were noted inside the prosthetic vascular wall. Three months after implantation, the inside was completely covered with an endothelial cell layer, and innumerable smooth muscle cells, fibroblasts and capillary vessels invaded the neoplastic vacular wall, and a new vascular wall was completed.

EXAMPLE 13

A vascular prosthesis was prepared as in Example 12, except that subcutaneous connective tissues were used. The prosthesis was implanted in the descending aorta of the same grown dog as in Example 12, and results similar to Example 11 were obtained.

EXAMPLE 14

In the method of depositing and capturing the tissue fragments of Example 12 on the vascular prosthesis substrate, the syringe used for applying a vacuum to the inner space was also filled with tissue fragment suspension, and by moving a piston positioned within the syringe, the tissue fragments were deposited and captured from both inside and outside of the substrate. When it was implanted in the descending aorta of a grown dog as in Example 12, the same results as in Example 12 were obtained.

The features of the vascular prosthesis substrate, the vascular prosthesis itself, and the manufacturing method of the invention may be summarized as follows.

1. The vascular prosthesis substrate of the invention is intended to deposit and capture tissue fragments and/or cells from inside or outside of the prosthesis by becoming entangled within and inside the wall of the prosthetic vascular substrate. Therefore, immediately after implanting this vascular prosthesis in the body of a mammal, the tissue fragments and/or cells will not separate, a new vascular wall is completed in three months after implantation, and the success rate of implantation is higher than in the prior art.

2. In the vascular prosthesis of the invention, since the tissue fragments are entangled within the prosthetic vascular wall, preclotting as required in the prior art is not necessary, and therefore it can be used in cases of emergency. Further, by using the tissues of the mammal receiving the prosthesis implant, the prosthesis is usable as an autograft, without fear of rejection.

3. The vascular prosthesis of the invention, which is unlike conventional vascular prostheses prepared by cell seeding because tissue fragments or cells are entangled in the prosthetic vascular wall from the inner side of the prosthesis or from the outer side. Thus, the vascular prosthesis of the present invention can be used, for example, in the surgical field.

4. The vascular prosthesis of the invention, when compared with conventional structure, is more quickly covered by endothelial cells after implantation, namely in about three weeks, and the vascular tissues are completed in about three months.

We claim:

1. A vascular prothesis comprising a porous substrate having a laminate structure of a higher porosity layer and a lower porosity layer, wherein the higher porosity layer has one of fragments of biological tissues, vascular cells and combinations thereof captured by its pores, and the lower porosity layer is impermeable to passage of the tissue cells and vascular cells therethrough.

2. The vascular prosthesis according to claim 1, wherein the lower porosity layer comprises insolublized collagen.

3. The vascular prosthesis according to claim 1, wherein the fragments of biological tissues comprise at least one of vascular tissue, connective tissues, fat tissues and muscular tissues, and the vascular cells comprise at least one of vascular endothelial cells, smooth muscle cells and fibroblast cells.

* * * * *